US008093352B2

(12) United States Patent
DeSousa et al.

(10) Patent No.: US 8,093,352 B2
(45) Date of Patent: Jan. 10, 2012

(54) POLYALKYLENE OXIDE POLYQUATERNARY AMMONIUM BIOCIDES

(75) Inventors: Ryan DeSousa, Fort Worth, TX (US); Nissanke L. Dassanayake, Fort Worth, TX (US); Howard Allen Ketelson, Dallas, TX (US)

(73) Assignee: Alcon Research, Ltd., Fort Worth, TX (US)

( * ) Notice: Subject to any disclaimer, the term of this patent is extended or adjusted under 35 U.S.C. 154(b) by 204 days.

(21) Appl. No.: 12/536,141

(22) Filed: Aug. 5, 2009

(65) Prior Publication Data
US 2010/0158853 A1 Jun. 24, 2010

Related U.S. Application Data

(60) Provisional application No. 61/086,371, filed on Aug. 5, 2008.

(51) Int. Cl.
C08G 65/00 (2006.01)
C08G 73/00 (2006.01)
A01N 33/12 (2006.01)
A01P 1/00 (2006.01)

(52) U.S. Cl. ........ 528/422; 528/392; 528/397; 528/425; 424/78.37

(58) Field of Classification Search .................. 528/392, 528/397, 422, 425; 424/78.37
See application file for complete search history.

(56) References Cited

U.S. PATENT DOCUMENTS

| | | | |
|---|---|---|---|
| 2,944,902 A | 7/1960 | Carroll et al. |
| 3,348,932 A | 10/1967 | Kukin |
| 3,349,032 A | 10/1967 | Krieg |
| 3,931,319 A | 1/1976 | Green et al. |
| 3,932,495 A | 1/1976 | Martinsson et al. |
| 4,001,432 A | 1/1977 | Green et al. |
| 4,012,446 A | 3/1977 | Green et al. |
| 4,027,020 A | 5/1977 | Green et al. |
| 4,054,542 A | 10/1977 | Buckman et al. |
| 4,110,263 A | 8/1978 | Lindemann et al. |
| 4,250,269 A | 2/1981 | Buckman et al. |
| 4,407,791 A | 10/1983 | Stark |
| 4,525,346 A | 6/1985 | Stark |
| 4,567,302 A | 1/1986 | Sivaramakrishnan |
| 5,145,643 A | 9/1992 | Dziabo et al. |
| 5,171,526 A | 12/1992 | Wong et al. |
| 5,277,901 A | 1/1994 | Vigh et al. |
| 5,300,287 A | 4/1994 | Park |
| 5,300,296 A | 4/1994 | Holly et al. |
| 5,342,620 A | 8/1994 | Chowhan |
| 5,451,398 A | 9/1995 | Vigh |
| 5,505,953 A | 4/1996 | Chowhan |
| 5,631,005 A | 5/1997 | Dassanayake et al. |
| 5,811,466 A | 9/1998 | Chowhan et al. |
| 6,051,611 A | 4/2000 | Kyba et al. |
| 6,143,799 A | 11/2000 | Chowhan et al. |
| 6,316,669 B1 | 11/2001 | Park et al. |
| 6,319,464 B1 | 11/2001 | Asgharian |
| 6,331,648 B1 | 12/2001 | Daly et al. |
| 6,365,636 B1 | 4/2002 | Chowhan et al. |
| 6,503,497 B2 | 1/2003 | Chowhan et al. |
| 6,664,294 B1 | 12/2003 | Park et al. |
| 6,849,253 B2 | 2/2005 | Chowhan et al. |
| 6,962,693 B2 | 11/2005 | Dassanayake et al. |
| 2004/0115160 A1 | 6/2004 | Salamone et al. |
| 2007/0292404 A1 | 12/2007 | Walsh et al. |
| 2008/0125543 A1 | 5/2008 | Kissel et al. |
| 2008/0153983 A1 | 6/2008 | Boeckh et al. |
| 2009/0143556 A1 | 6/2009 | Schorzman et al. |

FOREIGN PATENT DOCUMENTS

| | | |
|---|---|---|
| DE | 199 48 413 | 4/2001 |
| EP | 0 214 850 | 3/1987 |
| EP | 0 724 622 | 8/1996 |
| WO | 96/06603 | 3/1996 |
| WO | 97/39088 | 10/1997 |
| WO | 97/39089 | 10/1997 |
| WO | 97/39091 | 10/1997 |
| WO | 99/32521 | 7/1999 |
| WO | 01/09223 | 2/2001 |
| WO | 01/85891 | 11/2001 |
| WO | 01/94002 | 12/2001 |
| WO | 02/09766 | 2/2002 |
| WO | 02/079282 | 10/2002 |

(Continued)

OTHER PUBLICATIONS

Bedells A. D. et al.; J. Chem. Soc. Faraday Trans., 1993, 89, 1235-1242.

(Continued)

Primary Examiner — Duc Truong
(74) Attorney, Agent, or Firm — Michael D. Rein

(57) ABSTRACT

Disclosed are polyquaternary ammonium polymers containing polyalkylene oxide groups according to formula (I) wherein $[A]_x$, $[B]_y$ and $[C]_z$ are poly(alkylene oxides) each independently selected from the group consisting of poly(ethylene oxide), poly(propylene oxide), and poly(butylene oxide); Z is selected from the group consisting of —$CH_2CH$=$CHCH_2$—, —$CH_2CH_2CH_2CH_2$—, —$CH_2$—$C$≡$C$—$CH_2$—, —$CH_2CH_2$—$O$—$CH_2CH_2$—, —$CH_2$—$N(CH_2CH_2)_2N$—$CH_2$—, —$CH_2CH(OH)CH(OH)CH_2$— and —$CH_2$—$C_6H_4$—$CH_2$—; R is —$(CR_1R_2)_mCR_3R_4$— wherein m is an integer from 0 to 3 and $R_1$, $R_2$, $R_3$ and $R_4$ are independently selected from the group consisting of H, $CH_3$ and $CH_2CH_3$; n is an integer from 1 to 30; x is either 0 or an integer from 2 to 20; y is an integer from 2 to 20; z is either 0 or an integer from 2 to 20; R' is a branched or unbranched alkyl group having from 1 to 3 carbon atoms and is optionally substituted by one or two hydroxyl groups; Q1 and Q2 are independently selected from the group consisting of —$CH_2CH$=$CHCH_2$—X, —$CH_2C$≡$C$—$CH_2$—X, —$N(R')_2$, —$N(R')_3$, —$N(R')(R'')$, and —$N(R')_2(R'')$, wherein X is a halogen atom and R'' is a benzyl group; and a stoichiometric amount of a pharmaceutically acceptable anion. Also disclosed are suitable methods of making the polymers, and methods of using the polymers.

20 Claims, No Drawings

FOREIGN PATENT DOCUMENTS

| WO | 03/023126 | 3/2003 |
|---|---|---|
| WO | 2005/063847 | 7/2005 |
| WO | 2006/014067 | 2/2006 |
| WO | 2006/108856 | 10/2006 |
| WO | 2006/108857 | 10/2006 |

OTHER PUBLICATIONS

Chaibundit C. et al.; Langmuir, 2000, 16, 9645-9652.

Kelarakis A. et al.; Macromolecules, 1998, 31, 944-946.

Mülbaier et al.; "First synthesis and oxidative properties of polymer-supported IBX", ARKIVOC 2003 (vi) 228-236 [online] [retrieved on Jul. 2, 2008] Retrieved from the Internet <URL: http://www.arkat-usa.org/get-file/19949/>.

Nace V. M.; J. Am. Oil Chem. Soc., 1996, 73(1), 1-8.

Sashiwa et al.; "Chemical modification of chitosan, Part 9: Reaction of N-carboxyethylchitosan methyl ester with diamines of acetal ending PAMAM dendrimers", Carbohydrate Polymers, 2002, 47:201-208.

Yang Y.-W. et al.; Langmuir, 1995, 11, 4703-4711.

Yang Z. et al.; Macromolecules, 1994, 27, 2371-2379.

Yu G.-E. et al.; Langmuir, 1996, 12, 3404-3412.

POLYALKYLENE OXIDE POLYQUATERNARY AMMONIUM BIOCIDES

CROSS-REFERENCE TO RELATED APPLICATION

The present application claims priority from U.S. Provisional Application Ser. No. 61/086,371, filed Aug. 5, 2008.

FIELD OF THE INVENTION

The present invention relates to biocidal polymers that incorporate both poly(alkylene oxide) and quaternary ammonium groups into the backbone or repeating group of the polymer. The poly(alkylene oxide) group may be composed of a single poly(ethylene oxide), poly(propylene oxide) or poly(butylene oxide) chain, or alternatively multiple blocks of poly(ethylene oxide), poly(propylene oxide) or poly(butylene oxide) chains. The poly(alkyleneoxide) group may be bonded directly to the quaternary ammonium group in the repeating group of the polymer, or there may be an intervening linker group. Poly(butylene oxide) is the preferred poly(alkylene oxide) group. The polymers of the present invention exhibit useful antimicrobial activity. The repeating combination of poly(alkyleneoxide) and quaternary ammonium groups in the backbone of the polymers results in improved compatibility with sensitive tissues and/or improved compatibility with other formulation components and materials, including contact lens and packaging materials. The compositions and methods of the present invention are typically used in connection with ophthalmic, nasal, otic and contact lens care applications.

BACKGROUND OF THE INVENTION

Biocides are chemical substances that are capable of killing or controlling various living organisms. Biocides have a variety of uses in modern society, for example, as disinfectants, in pest control, in food for feedstock or food handling and preparation, as preservatives for wood and other materials, and in water systems. The Biocidal Products Directive 98/8/EC (BPD), classifies biocides into 23 different product types (i.e. application categories). Biocides are frequently added to other materials, notably liquids, so as to provide protection of that material from unwanted microorganisms.

The development of new and useful biocides requires consideration of many elements such as the following: the type(s) of organism whose control is desired; the manner in which the biocide is to be deployed; the costs of preparing and delivering the biocide; environmental or disposal issues; and so on. Depending on the potential use(s) envisioned, primary considerations are likely to include both its potency against the organisms targeted, as well as its biocompatibility, e.g. lack of toxicity against the humans or animals which may come into contact with it. Biocides may have a broad or narrow spectrum of activity. Biocides may be inorganic or organic depending on their intended use.

Many of the organic biocides in current use in the pharmaceutical field are based on molecules having a relatively limited variety of functional groups, including groups such as quaternary ammoniums, biguanides, primary, secondary or tertiary amines, amine-N-oxides and amides. These functional groups impart varying degrees of hydrophilicity to the molecules in which they are incorporated. In addition to these functional groups, broad spectrum biocides may require hydrophobic elements in order to penetrate biological membranes and achieve their full potency. Hydrophobicity in biocides can be achieved through incorporation of long chain hydrocarbons into the structure of the molecule. It is known that long chain hydrocarbons, when included into the structure of molecules containing biocidal groups, can improve the activity of the biocide. Thus, many organic biocides have both a lipophilic and hydrophilic component. Discovery of biocides that provide a desired balance between lipophilicity and hydrophilicity of a biocide for its field of use is a desirable result, and this balance can depend on the nature of the composition in which the biocide resides as well as the circumstances of its use. In the case of compositions intended for use in and around the eyes and for treating contact lens, such a balance can be highly challenging due in part to the extreme sensitivity of the eye to potential sources of irritation.

Although necessary for the effectiveness of the organic biocide, hydrophobicity can also cause damage to mammalian cells. Certain biocides used in conjunction with contact lens care and/or disinfection, in particular biocidal groups with long chain hydrocarbons, are known to cause a number of problems, including, for example, adsorption onto the surfaces of contact lenses or lens cases, which may lead to irritation to the wearer as a result of such adsorption, and loss of biocide available for disinfection. Conversely, biocides that are excessively hydrophilic tend to have diminished antimicrobial activity.

U.S. Pat. No. 3,931,319 (Jan. 6, 1976), U.S. Pat. No. 4,001,432 (Jan. 4, 1977) and U.S. Pat. No. 4,012,446 (Mar. 15, 1977), all issued to Green, et al., disclose a group of high molecular weight "capped" linear polymeric quaternary ammonium compounds found to be effective microbiocides (antimicrobials). The Green, et al. compounds are "capped" in the sense that both ends of the chains terminate in quaternary ammonium moieties. In a continuation-in-part application, now U.S. Pat. No. 4,027,020 (May 31, 1977), Green, et al. disclose a process for making randomly capped linear polymeric quaternary ammonium compounds; that is, the polymers produced by the improved process include those with very short chain lengths as well as those having relatively long chain lengths. These compounds were also found to have antimicrobial activity.

U.S. Pat. No. 4,407,791 (Oct. 4, 1983) and U.S. Pat. No. 4,525,346 (Jun. 25, 1985), both issued to Stark, disclose disinfecting solutions for contact lenses, wherein the aqueous solutions contain the Green, et al. polymers, including the compound commercially known as Onamer M® or PolyQuad®.

U.S. Pat. No. 4,110,263 (Lindemann et al.) describes mild cleansing compositions containing alkyleneoxylated bisquaternary ammonium compounds.

WIPO Publication No. 96/06603 (Park et al.) describes polyalkyene oxide containing quaternary ammonium antimicrobial agents.

U.S. Pat. No. 5,145,643 (Dziabo et al.) describes nonoxidative ophthalmic compositions and methods for preserving and using same.

The existing art notwithstanding, there still exists a need for biocides with one or any combination of the following: an effective balance of hydrophobic and hydrophilic elements; useful antimicrobial activity; non-irritating; low toxicity; compatibility with the materials and tissue with which they come into contact. The present invention is directed to achieving these and other aims.

SUMMARY OF THE INVENTION

The present invention is directed to new biocidal polymers that incorporate both poly(alkylene oxide) and quaternary ammonium groups into the backbone or repeating group of the polymer. The poly(alkylene oxide) group may be composed of a single poly(ethylene oxide), poly(propylene oxide) or poly(butylene oxide) chain, or alternatively multiple blocks of poly(ethylene oxide), poly(propylene oxide) or poly(butylene oxide) chains. The poly(alkyleneoxide) group may be bonded directly to the quaternary ammonium group in the repeating group of the polymer, or there may be an intervening linker group. Poly(butylene oxide) is the preferred poly(alkylene oxide) group.

The present invention is further directed to pharmaceutical compositions comprising at least one of the polymers of the present invention. In a preferred embodiment, one or more of the polymers of the present invention are included in ophthalmic compositions that comprise at least one of the polymers of the present invention and an ophthalmically acceptable vehicle.

The present invention is also directed to the use of the polymers of the present invention as biocides. In a preferred embodiment of the present invention, the polymers of the present invention are used as biocides in ophthalmic or contact lens care compositions. In a particularly preferred embodiment of the present invention, the polymers of the present invention are used to enhance antimicrobial activity, particularly when used in combination with borate/polyol systems or with known biocides such as Polyquad® or Aldox® (Al-6289).

Without wishing to be bound by theory, it is presumed that the poly(alkylene oxide) group in general, and in particular the poly(butylene oxide) group when present, impart a preferred balance of hydrophobic and hydrophilic qualities. This allows the polymers of the present invention to substantially retain useful biocidal efficacy, similar to the long chain hydrocarbons of known biocides, while ameliorating or reducing the undesirable attributes of hydrophobicity such as damage to mammalian cells. The greater solubility in water of the polymers of the present invention as compared to their alkyl or alkylene chain counterparts provides additional beneficial properties when the polymers of the present invention are incorporated into compositions that contact polymers (e.g. the polymers of contact lenses or the polymers of eyedrop bottles) and biological surfaces. Among the benefits of the polymers of the present invention, which incorporate at least one poly (alkyleneoxide) group in the polymer chain, are one or more of the following: (1) reduced toxicity; (2) less irritating to sensitive eye, nose or ear tissues; (3) reduced contact lens uptake and/or release; and (4) improved stability when containerized.

Advantageously, the properties of the polymers of the present invention may be tuned to optimize their lipophilic/hydrophilic balance depending on the particular intended application. This is accomplished principally by either varying the block length, or by varying the relative ratio of poly (alkylene oxide) groups if more than one type of group is present. For example, in an embodiment comprising both poly (butylene oxide) and poly (ethylene oxide) blocks, the relative ratio, or block size, of poly (butylene oxide) and poly (ethylene oxide) may be varied. The multiple parameters available for tuning permit considerable control over the properties the polymers of the present invention.

As utilized herein, the following abbreviations and terms, unless otherwise indicated, shall be understood to have the following meanings:

The abbreviation "PBO" means poly (butylene oxide).
The abbreviation "PPO" means poly (propylene oxide).
The abbreviation "PEO" means poly (ethylene oxide).
The abbreviation "PEO-PBO-PEO" means poly(ethylene oxide)-poly(butylene oxide)-poly(ethylene oxide).
The abbreviation "(EO)m(BO)n(EO)m" means ethylene oxide-butylene oxide-ethylene oxide.
The abbreviation "PHMB" means polyhexamethylene biguanide.
The abbreviation "mOsm/kg" means milliosmoles/kilogram of water.

The term "pharmaceutically acceptable anion" refers to anions of organic and inorganic acids which provide non-toxic salts in pharmaceutical preparations. Examples of such anions include chloride, bromide, iodide, sulfate, methylsulfate, phosphate, carbonate, and acetate.

The term "preservation-effective amount" means an amount of an antimicrobial agent effective in producing the desired effect of preserving the solutions described herein from microbial contamination, preferably an amount which, either singly or in combination with one or more additional antimicrobial agents, is sufficient to satisfy the preservative efficacy requirements of the United States Pharmacopoeia ("USP").

The term "disinfection-effective amount" means an amount of antimicrobial agent effective in producing the desired effect of disinfecting contact lenses by substantially reducing the number of viable microorganisms present on the lenses, preferably an amount which, either singly or in combination with one or more additional antimicrobial agents, is sufficient to satisfy one or more of the relevant requirements or standards of the FDA, ISO, ANSI, EU or Japan or comparable standard-issuing authority.

The term "ophthalmically acceptable vehicle" means a pharmaceutical composition having physical properties (e.g., pH and/or osmolality) that are physiologically compatible with ophthalmic tissues.

DESCRIPTION OF THE INVENTION

The novel biocides of the present invention comprise a polymer of the formula

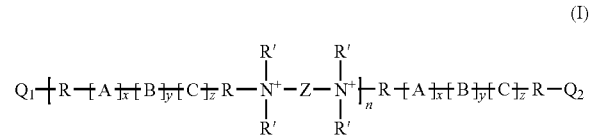

(I)

wherein $[A]_x$, $[B]_y$ and $[C]_z$ are poly(alkylene oxides) each independently selected from the group consisting of poly(ethylene oxide), poly(propylene oxide), and poly (butylene oxide); Z is selected from the group consisting of —CH$_2$CH=CHCH$_2$—, —CH$_2$CH$_2$CH$_2$CH$_2$—, —CH$_2$—C≡C—CH$_2$—, —CH$_2$CH$_2$—O—CH$_2$CH$_2$—, —CH$_2$—N(CH$_2$CH$_2$)$_2$N—CH$_2$—, —CH$_2$CH(OH)CH(OH)CH$_2$— and —CH$_2$—C$_6$H$_4$—CH$_2$—; R is —(CR$_1$R$_2$)$_m$CR$_3$R$_4$— wherein m is an integer from 0 to 3 and R$_1$, R$_2$, R$_3$ and R$_4$ are independently selected from the group consisting of H, CH$_3$ and CH$_2$CH$_3$; n is an integer from 1 to 30; x is either 0 or an integer from 2 to 20; y is an integer from 2 to 20; z is either 0 or an integer from 2 to 20; R' is a branched or unbranched alkyl group having from 1 to 3 carbon atoms and is optionally substituted by one or two hydroxyl groups; Q1 and Q2 are independently selected from the group consisting of —CH$_2$CH=CHCH$_2$—X, —CH$_2$C≡C—CH$_2$—X, —N(R')$_2$, —N(R')$_3$, —N(R')$_2$(R"), and —N(R')$_2$(R"), wherein X is a halogen atom and R" is a benzyl group; and a stoichiometric amount of a pharmaceutically acceptable anion.

Preferred polymers of the present invention are those of formula (I) wherein at least one of [A]$_x$, [B]$_y$ and [C]$_z$ is poly(butylene oxide); R' is methyl; and Z is —CH$_2$CH═CHCH$_2$—. Most preferred are polymers of formula (I) wherein [B]$_y$ is poly(butylene oxide); R' is methyl; x and z are 0; y is 6; R is —(CR$_1$R$_2$)$_m$CR$_3$R$_4$—; m is 2; Z is —CH$_2$CH═CHCH$_2$— and R1, R2, R3 and R4 are H.

The degree of polymerization, represented in the above formula by x, y, z and n, is an expression of the number of structural units in a given polymer molecule. This number typically represents the average degree of polymerization, as all the molecules in a given sample will not have the same exact number of structural units. However, as procedures for making polymers with exact molecular weights are available, and such polymers may be purchased from commercial sources, or obtained via contract synthesis, the polymers of the present invention may employ the use of polymers or polymer chains with an exact molecular weight, where there is not average number or distribution of molecular weights. While not necessarily exact, very narrow distributions are also possible and are preferred over broader distributions. Where x or z are 0, then there is only one poly(alkylene oxide) chain present.

The polymers of the present invention are preferably prepared by way of intermolecular condensation reactions. Two such routes to the polymers of the present invention are summarized by way of representative examples as depicted in the two reaction schemes designated Scheme I and II as shown below.

In the first of these routes, an alkylene oxide oligomer of known length with alcohol termini is converted to a dihalogenated poly(alkylene oxide) oligomer, as depicted in the first reaction sequence of Scheme I. The dihalopolyoxyalkylene oligomer is then condensed with a bis-dialkyldiaminebutylene to provide the polymers of formula (I), as shown in the second reaction in Scheme I.

Scheme I:

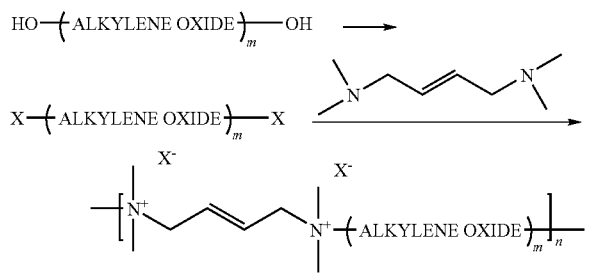

In Scheme I, if the dihalogenated oligomer is in molar excess, then the resulting polymer chain will terminate with halogen atoms, which may then be further reacted with various endgroups, for example, mono-, di- or tri-alkylamines, or simply hydrolyzed. If, instead, the dialkyldiamine butylene is in excess, then the resulting polymer is expected to terminate with tertiary amine groups.

The poly(alkylene oxide) starting materials may, in various embodiments of the invention, be in the form of mono-, di-, or tri-blocks of poly(ethylene oxide), polypropylene oxide) or poly(butylene oxide). These block copolymers may be prepared by the application or adaptation of known methods described in the literature, for example, as described in Nace, V. M. J. Am. Oil Chem. Soc. 1996, 73, 1; Yang, Z.; Pickard, S.; Deng, N.-J.; Barlow, R. J.; Attwood, D.; Booth, C. Macromolecules 1994, 27, 2371; Yang, Y.-W.; Deng, N.-J.; Yu, G.-E.; Zhou, Z.-K.; Attwood, D.; Booth, C. Langmuir 1995, 11, 4703; Yu, G.-E.; Yang, Y.-W.; Yang, Z.; Attwood, D.; Booth, C.; Nace, V. M. Langmuir 1996, 12, 3404; Chaibundit, C.; Mai, S.-M.; Heatley, F.; Booth, C. Langmuir 2000, 16, 9645; Bedells, A. D.; Arafeh, R. M.; Yang, Z.; Attwood, D.; Heatley, F.; Pedget, J. C.; Price, C.; Booth, C. J. Chem. Soc., Faraday Trans. 1993, 89, 1235; and Kelarakis, A.; Havredaki, V.; Yu, G.-E.; Derici, L.; Booth, C. Macromolecules 1998, 31, 944, the entire contents of each of which are hereby incorporated in the present application by reference.

As an example, diblock copolymer including both a PEO and a PBO chain, i.e., a PEO-PBO block copolymer, may be synthesized using a well-defined polyethylene glycol (PEG) polymer by controlled addition of oxybutylene to the primary hydroxyl group of the PEG polymer. For example, the PEO-PBO di-block copolymer (EO)$_{41}$(BO)$_{10}$ may be prepared by the following sequential anionic polymerization technique:

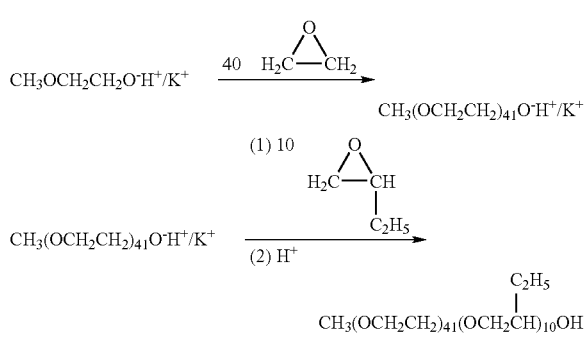

Other variations of the block chemistry structure may also be prepared, using techniques and methods readily available to and adaptable by those skilled in art. For example, such techniques and methods can be used to develop the following reaction process for the preparation of tri-block copolymers of the form (EO)m(BO)n(EO)m.

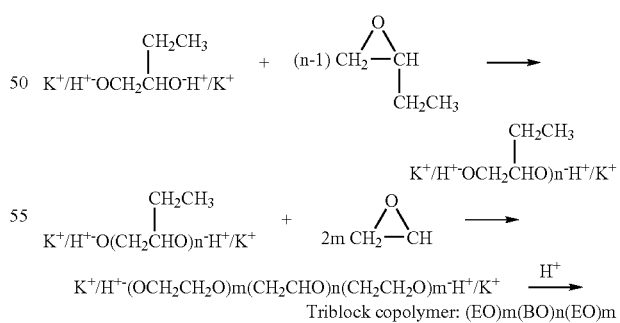

An example of the reaction sequence shown generally in Scheme I is now be depicted in further detail. In this example, a polybutylene oxide derivative of length y+2 (I-A) is reacted with either phosphorous trichloride and 1,8-diazabicyclo[5.4.0]undecene-7 (DBU) or thionyl chloride and DBU to convert the hydroxyl endgroups to chlorine (I-B).

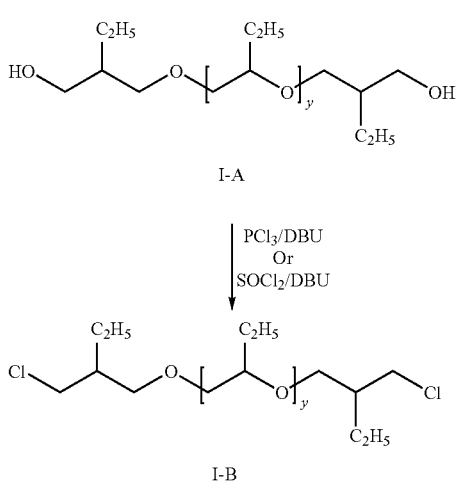

I-A

I-B

In the polymerization step, the dihalogen derivative I-B is then reacted with tetrasubstituted butylene diamine (for example, N,N,N',N'-tetramethyl-2-butene-1,4-diamine, available from Sigma-Aldrich, St. Louis Mo. 63103) to form the polyquaternary polybutylene oxide I-C as shown below.

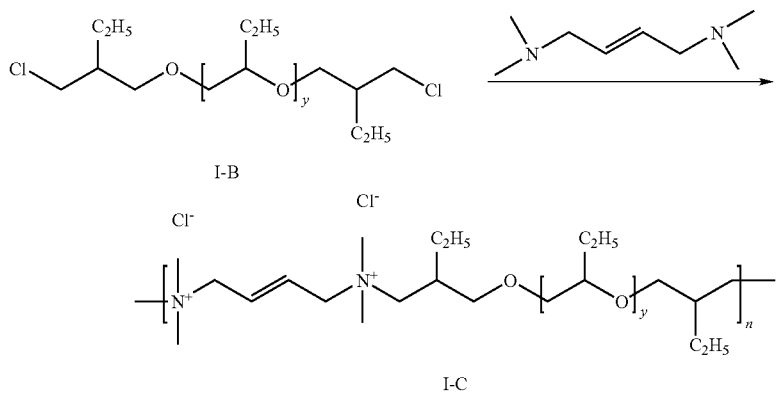

I-B

I-C

The second of two exemplary condensation reaction routes to the polymers of formula (I) is now described. At the present time, this second route is the preferred method of preparing the polymers of the present invention based on increased yields. In this second route, depicted in Scheme II as shown below, a bis-dialkyldiaminepolyalkyleneoxide is condensed with a dihalobutene to provide the polymers of formula (I).

Scheme II:

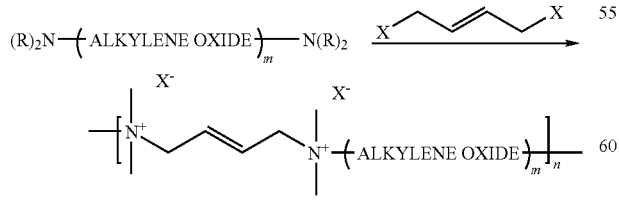

Scheme II depicts a condensation reaction of a dihaloalkylene, e.g., 1,4-dichoro-2-butene (available from Sigma-Aldrich, St. Louis Mo. 63103 as trans-1,4-dichloro-2-butene) with a roughly molar equivalent quantity of a bis-tertiaryamine-poly(alkyleneoxide). If the bis-tertiaryamine-poly(alkyleneoxide) is in slight molar excess, then the resulting chain terminates with the diamine group. If instead there is a slight molar excess of the dihalogen reactant, then the resulting halogen termini may be removed via hydrolysis, reduction, or capping with an appropriate endgroup, for example, a monotertiary amine. This route is analogous to the synthesis of polyquaternium-1 and related polymeric ammonium compounds as described in U.S. Pat. No. 3,931,319 (Green et al.), the contents of which are hereby incorporated into the present specification in their entirety. The two-step synthetic approach described in the '319 patent begins with the condensation reaction of 1,4-dihalo-2-butene with a slightly less than molar quantity of a bis-tertiaryamine. The unreacted dihalo reagent is separated from resulting halogen-terminated polymer chain and a calculated quantity of tertiary amine is added to "cap" the chain with quaternary ammonium termini.

The bis-tertiaryamine-poly(alkyleneoxide) starting material depicted in Scheme II is obtained using known synthetic methods. For example, the bis-tertiaryamine-poly(alkyleneoxide) is obtained via amidation and then reduction of a corresponding carboxylic acid resulting from oxidation of a poly (alkyleneoxide) starting material. If the poly (alkyleneoxide) group in the starting material does not have primary alcohols end groups, as may the case with certain poly (butylene oxides), for example, it would not be suitable for direct conversion to the carboxylic acid. In this case, the poly (alkylene oxide) must be provided with a primary alcohol end group. In one embodiment of the present invention, the poly (butylene oxide) starting material is bracketed with poly (ethylene oxide) groups, resulting in a tri-block type material which may then be converted into the diamine. A representative PEO-PBO-PEO block to be used as a starting material in the preparation of a bis-tertiaryamine-poly(alkyleneoxide) may be prepared in the following manner:

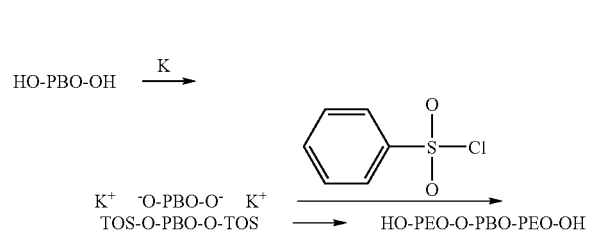

In another embodiment of the present invention, the poly (alkylene oxide) starting material is bracketed with small organic linking groups. Some examples using this second alternative are now described. In the following example, poly(butylene oxide) is prepared for use as a starting material in the preparation of a bis-tertiaryamine-poly(butylene oxide) by conversion to the corresponding dinitrile, as indicated by the following process:

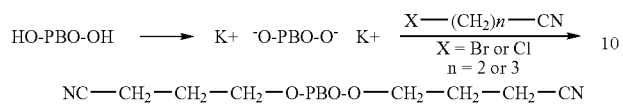

The dinitrile is then converted to the carboxylic acid using standard organic synthetic methods, for example, the methods described in Newcome et al., Org. Prep. Proc. Int. 1996, 28, 242 and also Newcome et al., J. Mat. Chem. 1997, 7(7) 1237, both of which are hereby incorporated into the present specification by reference.

An alternative approach to preparing a poly(butylene oxide) block for coupling involves the use of a bromo- or chloro-ester reagent as depicted below:

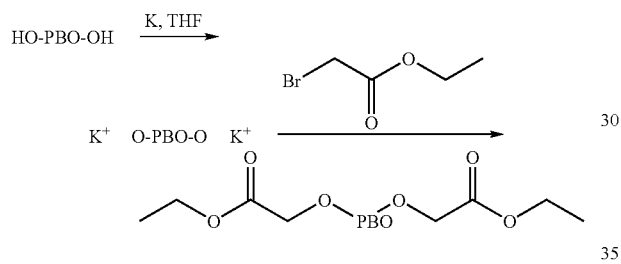

If milder reaction conditions are desired due to the acidic properties of the alpha protons in the acetate, a milder base may be formed, substituting, for example, $K_2CO_3$ for potassium. Alternatively, the corresponding diester may be formed without a catalyst by simply mixing the two reactants in a suitable solvent, for example, THF, as described in Mülbaier et al.: First synthesis and oxidative properties of polymer-supported IBX, ARKIVOC 2003 (vi) 228-236 [online] [retrieved on 2008-07-02] Retrieved from the Internet <URL: http://www.arkat-usa.org/get-file/19949/>, hereby incorporated by reference into the present specification.

The diesters are then reacted with a disubstituted amine, as depicted below:

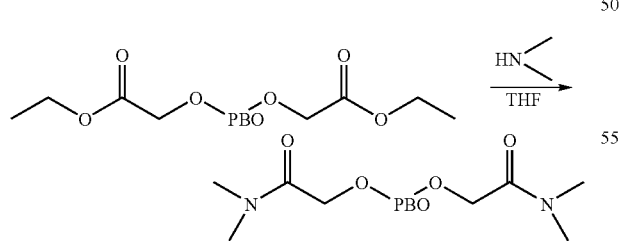

This reaction may be carried out using THF as solvent without any catalyst, as described in Sashiwa et al.: Chemical modification of chitosan, Part 9: Reaction of N-carboxyethylchitosan methyl ester with diamines of acetal ending PAMAM dendrimers, Carbohydrate Polymers 2002, 47:201-208, the contents of which are hereby incorporated into the present specification by reference. If a faster reaction is desired, the following alternative reaction sequence may be employed using a corresponding diacid as the starting material:

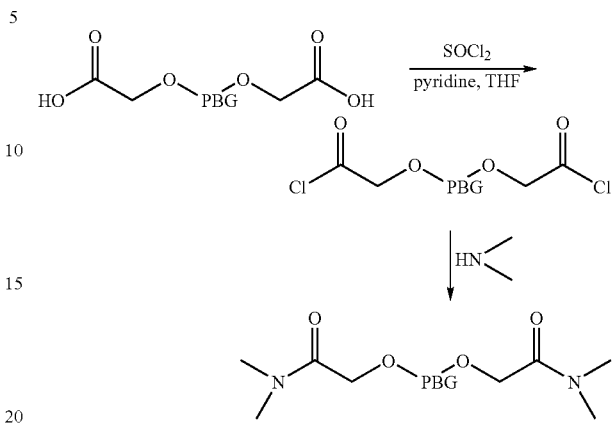

The resulting diamides can be reduced to amine using a suitable catalytic reducing agent, for example, $Ru_3(CO)_7$, $Zn$—$CH_3CH_2OH$, $MoO_2Cl_2$, $LiAlH_4$, $LiAlH_4/AlCl_3$ or Borane-THF complex. As an incomplete reduction may generate undesirable aldehydes, the Borane-THF complex is considered to be the best choice among the presently listed alternatives.

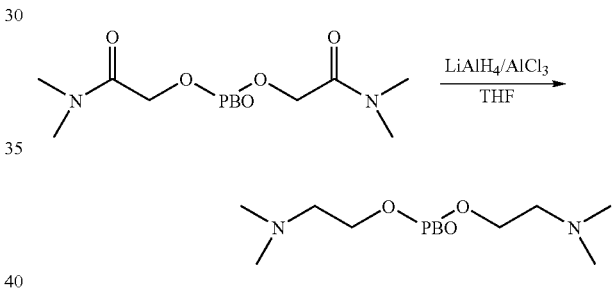

To complete the process of forming the polyquaternium polymers of the invention, the diamines are reacted with dichlorobutene. While water is the preferred solvent for this reaction, other solvents may be suitable and choice of solvent and bulk reaction conditions may be optimized through routine experimentation.

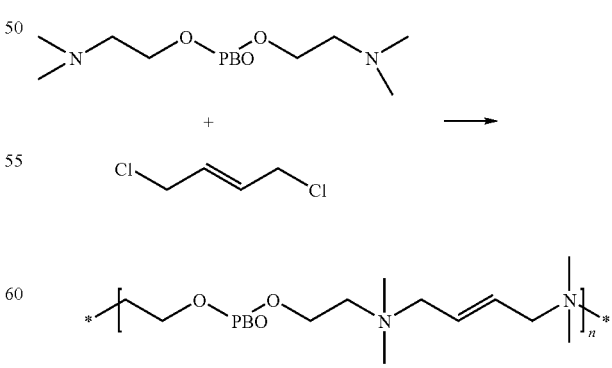

In the case where the dihalobutene or equivalent is in excess of the diamine, polymerization would typically continue until the diamine is exhausted, resulting in polymeric chains terminating in halogen atoms. To "cap" the polymer chain, a suitable "capping" group, for example, a tertiary amine, may be added to the polymeric residue. An alternative capping method is based on a single-step synthesis as described in U.S. Pat. No. 4,027,020 (Green et al.), the disclosure of which is hereby incorporated into the present specification by reference. In this method, a slight molar excess of diamine to dihalobutene is used, and a capping group, for example, a tertiary amine, is added to the initial reaction mixture. This typically will result in a mixture of polymers of differing chain length, as both chain propagation and chain termination proceed competitively.

The synthesis of a representative polymer of the present invention where x and z are 0, $[B]_y$ is poly(butylene oxide) where y is 6, R is $-(CR_1R_2)_m CR_3R_4-$, m is 2, Z is $-CH_2CH=CHCH_2-$ and R1, R2, R3 and R4 are H according to the general approach outlined above as Scheme II is now depicted in further detail below and in Example 3.

Step 1: Synthesis of PBO Precursors Via Anionic ROP of Butylene Oxide Monomer:

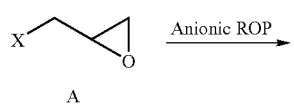

A

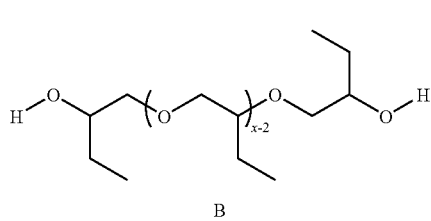

B

PBO precursor x = 6

Step 2: End Functionalization of the PBO Precursor:

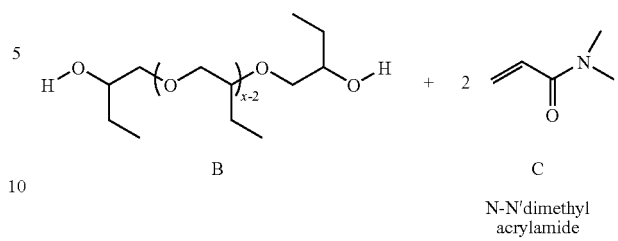

B    C

N-N'dimethyl acrylamide

Michael reaction ↓

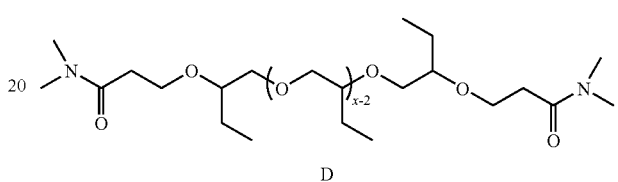

D

BH3-THF | Reduction ↓

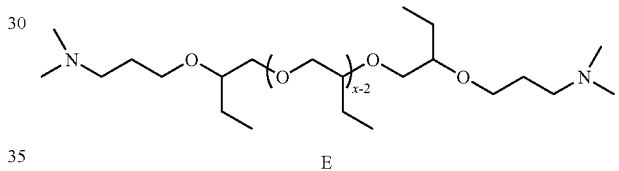

E

Step 3: Step Growth Polymerization via quaternization reaction.

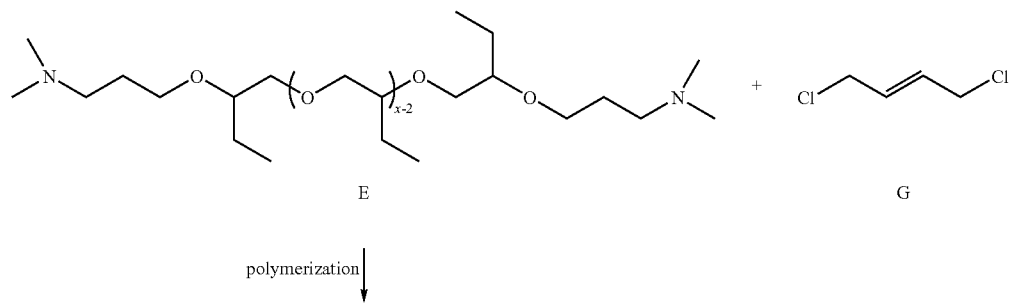

E    G polymerization ↓

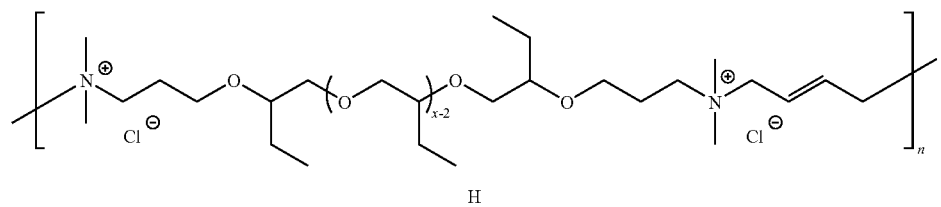

H

The polymers of the present invention may be used as antimicrobials in various compositions, particularly as disinfectants in contact lens care products and as preservatives in other types of ophthalmic compositions, such as artificial tears, or topical pharmaceutical preparations. The types of compositions which may be preserved by the polymers of formula (I) include: ophthalmic pharmaceutical compositions, such as those described below; otic pharmaceutical compositions, such as topical compositions used in the treatment of bacterial infections or inflammation of the ear; dermatological compositions, such as anti-inflammatory compositions, as well as shampoos and other cosmetic compositions; and various other types of pharmaceutical compositions. In general, the polymers of the present invention will be present in the compositions at a concentration between about 0.00001 and 1.0 percent by weight (wt %). If used as a disinfectant, the polymers are preferably present at a concentration of between about 0.0005 and 0.5 wt %; if used as a preservative, the polymers are present at a concentration between about 0.00005 and 0.05 wt %. It is preferred that the polymers are present at a concentration of between 0.001 and 0.05 wt % if used as a disinfectant and between 0.0001 and 0.01 wt % if used as a preservative.

Compositions containing the polymers of the present invention may additionally contain other components, for example, buffers, tonicity adjusting agents, chelating agents, surfactants, solublizers, active pharmaceutical agents, preservatives, pH adjusting agents and carriers.

In the case of contact lens and ophthalmic compositions that contain the polymers of the present invention, for example, various agents are typically added to enhance compatibility with the eye. To avoid stinging or irritation it is important that the solution possess a tonicity and pH within the physiological range, e.g., 200-350 mOsmole/kilogram for tonicity and 6.5-8.5 for pH. To this end, various buffering and osmotic agents are often added. The simplest osmotic agent is sodium chloride since this is a major solute in human tears. In addition propylene glycol, lactulose, trehalose, sorbitol, mannitol or other osmotic agents may also be added to replace some or all of the sodium chloride. Also, various buffer systems such as citrate, phosphate (appropriate mixtures of $Na_2HPO_4$, $NaH_2PO_4$, and $KH_2PO_4$), borate (boric acid, sodium borate, potassium tetraborate, potassium metaborate and mixtures), bicarbonate, and tromethamine and other appropriate nitrogen-containing buffers (such as ACES, BES, BICINE, BIS-Tris, BIS-Tris Propane, HEPES, HEPPS, imidazole, MES, MOPS, PIPES, TAPS, TES, Tricine) can be used to ensure a physiologic pH between about pH 6.5 and 8.5. Borate and polyol systems may also be used to provide buffering, to enhance antimicrobial activity, or to provide both buffering and an enhancement of antimicrobial activity, or other useful properties to the compositions of the invention. The borate and polyol systems which may be used include those described in U.S. Pat. Nos. 6,849,253; 6,503,497; 6,365,636; 6,143,799; 5,811,466; 5,505,953; and 5,342,620; the entire contents of each are hereby incorporated in the present specification by reference.

In addition to the polymers of formula (I) described above, compositions containing polymers of the present invention may contain also one or more additional antimicrobial agents. The invention is not limited relative to the types of additional antimicrobial agent that may be utilized. The preferred biocides include: polyhexamethylene biguanide polymers ("PHMB"), polyquaternium-1, and the amino biguanides described in U.S. Pat. No. 6,664,294, the entire contents of which are hereby incorporated in the present specification by reference.

Amidoamines, amino alcohols, and borate/polyol complexes may also be utilized to enhance the antimicrobial activity of the compositions described herein. Preferred amidoamines include myristamidopropyl dimethylamine ("MAPDA") and related compounds described in U.S. Pat. No. 5,631,005 (Dassanayake, et al.) Preferred amino alcohols include 2-amino-2-methyl-1-propanol ("AMP") and other amino alcohols described in U.S. Pat. No. 6,319,464 (Asgharian). The entire contents of Dassanayake, et al. and Asgharian are hereby incorporated in the present specification by reference.

The above-described compositions may be used to disinfect contact lenses in accordance with processes known to those skilled in the art. More specifically, the lenses will first be removed from the eyes of the patients, and then will be immersed in compositions for a time sufficient to disinfect the lenses. This immersion will typically be accomplished by means of soaking the lenses in a solution overnight (i.e., approximately six to eight hours). The lenses will then be rinsed and placed in the eye. Prior to immersion in the disinfecting compositions, the lenses will preferably also be cleaned and rinsed.

All of the above-described compositions will be formulated so as to be compatible with the eye and/or contact lenses to be treated with the compositions. As will be appreciated by those skilled in the art, the ophthalmic compositions intended for direct application to the eye will be formulated so as to have a pH and tonicity, which are compatible with the eye. This will normally require a buffer to maintain the pH of the composition at or near physiologic pH (i.e., 7.4) and may require a tonicity agent to bring the osmolality of the composition near to 300 mOs/kg.

The formulation of compositions for disinfecting and/or cleaning contact lenses will involve similar considerations, as well as considerations relating to the physical effect of the compositions on contact lens materials and the potential for binding or absorption of the components of the composition by the lens.

The compositions and methods of the present invention may be used in conjunction with various types of contact lenses, including both lenses generally classified as "hard" and lenses generally classified as "soft".

The following examples further illustrate certain embodiments of the invention. These examples are provided to aid in the understanding of the invention and are not to be construed as limitations thereof.

EXAMPLE 1

The polymer with formula I-C is suitably obtained by a synthetic method as described below.

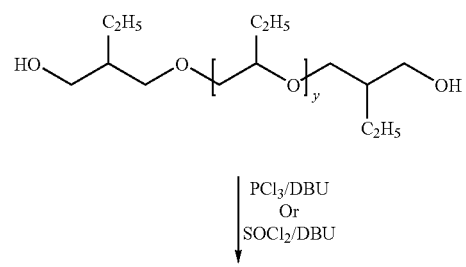

-continued

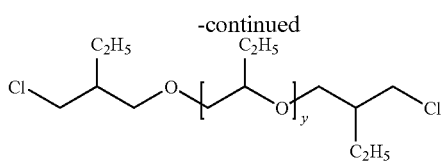

Add thionyl chloride (12 mmol) or phosphorous trichloride (12 mmol) to a round bottom flask fitted with a condenser containing the polymer I-A (12 mmol) in methylene dichloride. (50 ml) and DBU. Reflux the mixture for about 4 hrs (monitor completion of reaction by TLC). Remove excess solvent and thionyl chloride under reduced pressure to obtain dichloride I-B.

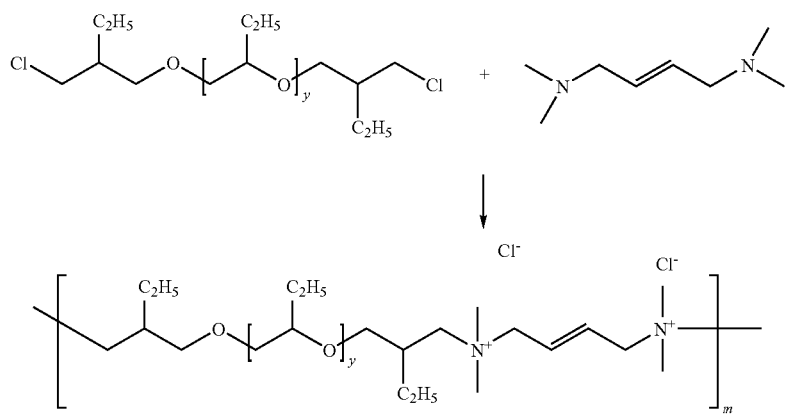

Dissolve 0.2 moles of 1,4-bis-dimethylamino-2-butene in 60 ml water in a round bottom flask fitted with a stirrer and reflux condenser. Add 0.205 moles of dichloride I-B slowly while stirring. Heat the reaction mixture while stirring and maintain the temperature at 60-70° C. for approximately six hours. The reaction progress may be determined by the analysis for the presence of ionic chloride. Evaporate water under vacuum and weigh the residue product I-C.

EXAMPLE 2

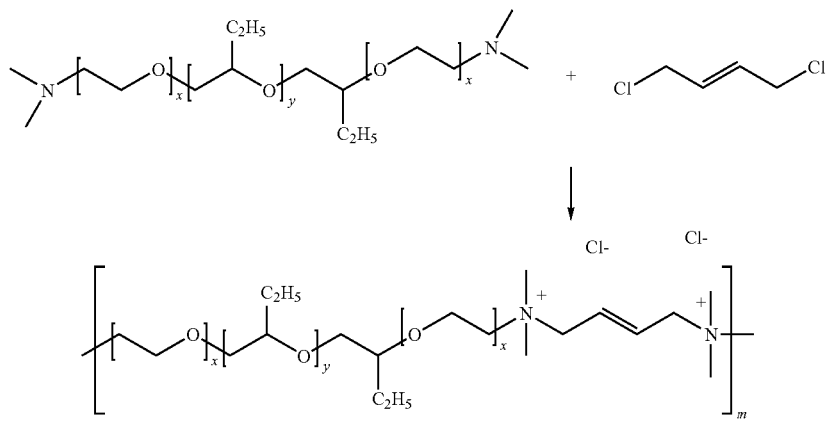

Dissolve 0.2 moles of the PEO-PBO-PEO dimethyl amine in 60 ml water in a round bottom flask fitted with a stirrer and reflux condenser. Add 0.205 moles of 1,4-dichloro-2-butene slowly while stirring. Heat the reaction mixture while stirring and maintain the temperature at 60-70° C. for six hours. The reaction time is determined by the analysis for the presence of ionic chloride. Evaporate water under vacuum and weigh the residue.

EXAMPLE 3

Preparation of Structure D

Poly(1,2-butylene oxide) or Poly(1,2-butylene glycol) (10.4 mmoles) was vacuum dried at 60° C. for 5 hrs. N,N-dimethylacrylamide (28.0 mmoles) was added, tetrahydrofuran (THF) as solvent (20 g) was added. The mixture was stirred under nitrogen. Potassium hydroxide powder (0.05 g) added. The system was stirred at room temperature for 20 hrs. The THF was rotavaporated. Hexane was added to stir. The mixture was transferred to a separation funnel. The mixture in hexane was washed 3 times to obtain the product in hexane. Then hexane was rotavaporated. The raw product was set to vacuum at 50° C. for 10 hrs to obtain product (D).

Structure D: 1H NMR (CDCl$_3$ solvent, Varian Unity 500 MHz NMR, 8 scans at 5 second delay time). Multi peaks at 0.9 ppm and peaks at 1.44 to 1.46 ppm are for PBO side chain group —CH$_2$—CH$_3$; multi peaks at 2.58 ppm is from PBO—O—CH$_2$—CH$_2$—CON(CH$_3$)$_2$; doublets at 2.9 and 2.99 ppm are from —CON(CH$_3$)$_2$; multi peaks from 3.2 to 3.6 ppm are from the backbone protons of PBO, —CH$_2$—CH(C$_2$H$_5$)—; the peaks at 3.77 and 3.85 ppm are from PBO—O—CH$_2$—CH$_2$—CON(CH$_3$)$_2$.

Preparation of Structure E

The product (D) (16.7 mmoles) was weighed into a 500 ml three neck flask. THF (20 ml) was added. Borane-tetahydrofuran (1M, 50 mmoles) was dropped into the flask in a period of 30 minutes, under nitrogen, then reflux for 2 hours. Then most of the THF was distilled out. Ethanol (70 ml) was added and set to reflux for 12 hours. After the solution is cooled to room temperature, sodium hydroxide solution (1N) was used to adjust the pH of the solution up to 11. Solid should be seen in the system. The solvent was rotavaporated from the filtered solution. The products was dissolved with ethyl acetate and washed with water 3 times. The solvents were rotavaporated to obtain product (E).

Structure E: 1H NMR (CDCl$_3$ solvent, Varian Unity 500 MHz NMR, 8 scans at 5 second delay time). Multi peaks at 0.9 ppm and peaks at 1.44 to 1.46 ppm are for PBO side chain group —CH$_3$—CH$_2$; Peaks around 1.74 ppm are from —PBO—O—CH$_2$—CH$_2$—CH$_2$—N(CH$_3$)$_2$; peaks around 2.33 ppm are from —PBO—O—CH$_2$—CH$_2$—CH$_2$—N(CH$_3$)$_2$ and the intense peak at 2.2 ppm is from —PBO—O—CH$_2$—CH$_2$—CH$_2$—N(CH$_3$)$_2$. Multi peaks from 3.2 to 3.7 ppm are from the backbone protons of PBO, —CH$_2$—CH(C$_2$H$_5$)— and —PBO—O—CH$_2$—CH$_2$—CH$_2$—N(CH$_3$)$_2$.

Preparation of Structure H

PBO-bis(dimenthylamine) (1.44 g, 2.25 mmol), 1,4-dichloro-2-butene (0.1767 g, 1.41 mmol) were weighed into a 50 ml flask, THF (1.7 g) was added. The solution was stirred at 60° C. to carry out the polymerization for more than 5 hours to obtain product (H). The molecular weight is increased with longer time.

Structure H: 1H NMR (Bruker 400 MHz, D2O) and 2D-1H-NMR (Bruker, 600 MHz, is D2O). Peaks around 0.9 ppm and 1.5 ppm are from the CH$_3$ and CH$_2$ side chain protons respectively of the butylene oxide units, peaks in the regions 3.4-3.5 ppm and 3.5 to 3.6 ppm are from the CH and CH$_2$ backbone protons of the butylene oxide units, i.e. —PBO—CH$_2$—CH(C$_2$H$_5$)—. Peak at around 2.06 ppm is from —PBO—O—CH$_2$—CH$_2$—CH$_2$—N$^{(+)}$ (CH$_3$)$_2$— and peaks in the regions 3.3 to 3.4 ppm and 3.6 to 3.7 ppm are from —PBO—O—CH$_2$—CH$_2$—CH$_2$—N$^{(+)}$(CH$_3$)$_2$, the doublet at around 3.05 ppm is from —PBO—O—CH$_2$—CH$_2$—CH$_2$—N$^{(+)}$ (CH$_3$)$_2$—, peak at 6.3 ppm are from the protons attached to the alkene, —CH$_2$HC=CH—CH$_2$—. The peak of the methylene groups attached to the alkene, CH$_2$HC=CH—CH$_2$—, are in the region 3.9 to 4.3 ppm.

EXAMPLE 4

A representative polymer of formula (I) wherein x and z are 0; [B]$_y$ is poly(butylene oxide), y is 6, R is —(CR$_1$R$_2$)$_m$CR$_3$R$_4$—, m is 2, R1, R2, R3 and R4 are H, R' is methyl and Z is —CH$_2$CH=CHCH$_2$—, designated here as PQDX6, was evaluated for preservative activity using a Stand Alone Test Procedure for Contact Lens Disinfecting Solutions (such as OPTI-FREE EXPRESS). The Stand Alone Test challenges a formulation with a standard inoculum of a representative range of microorganisms and establishes the extent of their viability loss at pre-determined time intervals comparable with those during which the formulation may be used. The test was based on guidelines and standards provided in the ISO 14729:2001 Standard: "Ophthalmic Optics-Contact Lens Care Products—Microbiological Requirements and Test Methods for Products and Regimens for Hygienic Management of Contact Lenses", and the FDA Guidelines: "Premarket Notification (510 k) Guidance Document for contact Lens Care Products (May, 1997)".

The Stand Alone test uses five test organisms (3 bacteria and 2 fungi): Bacteria: *Staphylococcus aureus, Pseudomonas aeruginosa, Serratia marcescens*, and fungi: *Candida albicans* (yeast) and *Fusarium solani* (mold). The testing described below was a Stand Alone Screen test (abbreviated Stand Alone test), using 3 test organisms: *S. aureus, S. marcescens*, and *C. albicans*.

To conduct the test, about $1^6$ (1 million) organisms were inoculated into 10 mL of the formulation being tested, mixed, and held at room temperature for 6 hours. Then, a 1 ml sample was withdrawn, diluted and plated with agar using a serial dilution pour-plate method. Both the dilution fluid and the agar contained neutralizing agents to stop the action of the antimicrobials. Then, the pour-plates (agar plates) were incubated at appropriate temperatures and times to recover the specific organisms being tested. After incubation, the agar plates were counted and recorded, and calculations were conducted to show the amount of kill or reduction of the numbers of organisms.

Example of calculations:

Initial Inoculum level=1.0×10$^6$(Log=6.0)

Count after 6hrs=1.0×10$^3$(Log=3.0)

Log Reduction@6hr=(6.0–3.0)=3.0 log reduction

As can be seen from the disinfection data, the representative polymer tested showed activity against bacteria in the concentration range between 5 and 50 ppm. Activity against fungi is seen only at the higher end of this concentration range. Three different lots of the representative polymer PQDX6 were prepared and from the disinfection screen results they all appear to be similar.

TABLE 1

| | Disinfection Screen data for PQDX6 (Lot #2 and #3) | | | | | | | | | | |
|---|---|---|---|---|---|---|---|---|---|---|---|
| | Concentration (% w/v) | | | | | | | | | | |
| Component | 14336-56A | 14336-56B | 14336-56C | 14336-56D | 14336-56E | 14336-56F | 14336-56G | 14336-56H | 14336-56I | 14336-56J | 14336-56K | OPTI-FREE ® Express ® MPDS$^a$ |
| PQDX6 #2 | | | | 0.0005 | 0.005 | | | | 0.0005 | 0.005 | | |
| PQDX6 #3 | | 0.0005 | 0.005 | | | | 0.0005 | 0.005 | | | | |
| Poly-quaternium-1 (Stepan) | | | | | | 0.001 | | | | | 0.001 | |

TABLE 1-continued

Disinfection Screen data for PQDX6 (Lot #2 and #3)

| | | | | | | | | | | | |
|---|---|---|---|---|---|---|---|---|---|---|---|
| Propylene Glycol | 0.5 | 0.5 | 0.5 | 0.5 | 0.5 | 0.5 | 0.5 | 0.5 | 0.5 | 0.5 | 0.5 |
| Boric Acid | 0.6 | 0.6 | 0.6 | 0.6 | 0.6 | 0.6 | 0.6 | 0.6 | 0.6 | 0.6 | 0.6 |
| Sodium Chloride | 0.32 | 0.32 | 0.32 | 0.32 | 0.32 | 0.32 | 0.32 | 0.32 | 0.32 | 0.32 | 0.32 |
| Tetronic 1304 | | | | | | | 0.05 | 0.05 | 0.05 | 0.05 | 0.05 |
| pH | 7.0 | 7.0 | 7.0 | 7.0 | 7.0 | 7.0 | 7.0 | 7.0 | 7.0 | 7.0 | 7.0 |

$Log_{10}$ Reduction of Survivors

| Microorganism | Time | 14336-56A | 14336-56B | 14336-56C | 14336-56D | 14336-56E | 14336-56F | 14336-56G | 14336-56H | 14336-56I | 14336-56J | 14336-56K | OPTI-FREE® Express® MPDS[a] |
|---|---|---|---|---|---|---|---|---|---|---|---|---|---|
| C. albicans $1.4 \times 10^{6b}$ | 6 | −0.1 | 0.0 | 0.7 | 0.0 | 0.8 | 2.2 | 0.0 | 0.5 | 0.0 | 0.8 | 2.2 | 3.7 |
| | 24 | 0.0 | 0.2 | 1.3 | 0.2 | 1.4 | 3.2 | 0.2 | 1.3 | 0.2 | 1.5 | 3.2 | <u>6.1</u> |
| S. marcescens $6.1 \times 10^5$ | 6 | −0.4 | 1.6 | 5.1 | 1.8 | <u>5.8</u> | 2.8 | 2.6 | <u>5.8</u> | 2.0 | <u>5.8</u> | 2.8 | 3.3 |
| | 24 | −0.4 | 3.2 | <u>5.8</u>[c] | 2.3 | <u>5.8</u> | <u>5.8</u> | 2.3 | <u>5.8</u> | 2.5 | <u>5.8</u> | 5.1 | 5.1 |
| S. aureus $1.8 \times 10^6$ | 6 | −0.1 | 2.1 | 4.2 | 2.3 | 4.8 | 4.4 | 3.0 | 4.4 | 3.0 | 4.9 | 5.1 | 2.0 |
| | 24 | 0.0 | 3.7 | <u>6.3</u> | 5.0 | <u>6.3</u> | 5.3 | 5.6 | <u>6.3</u> | 5.3 | <u>6.3</u> | <u>6.3</u> | 4.2 |

14040:058
[a] Lot 136624F, exp. April 2010
[b] Inoculum control count
[c] Underlined number indicates no survivors (<10 CFU/mL) recovered

TABLE 2

Disinfection Screen data for PQDX6 (Lot 2 and 4)

% wt/% vol

| Component | 14762-27A | 14762-27B | 14762-27C | 14762-27D | 14762-27E | 14762-27F | 14762-27G | 14762-27H | 14762-27I | 14762-27J | OPTI-FREE® Express®[a] |
|---|---|---|---|---|---|---|---|---|---|---|---|
| Propylene Glycol | 0.5 | 0.5 | 0.5 | 0.5 | 0.5 | 0.5 | 0.5 | 0.5 | 0.5 | 0.5 | |
| Boric Acid | 0.6 | 0.6 | 0.6 | 0.6 | 0.6 | 0.6 | 0.6 | 0.6 | 0.6 | 0.6 | |
| Sodium Chloride | 0.32 | 0.32 | 0.32 | 0.32 | 0.32 | 0.32 | 0.32 | 0.32 | 0.32 | 0.32 | |
| Tetronic 1304 | 0.05 | 0.05 | 0.05 | 0.05 | 0.05 | 0.05 | 0.05 | 0.05 | 0.05 | 0.05 | |
| PQDX6 #2 | — | 0.0005 | 0.0025 | 0.005 | — | — | — | — | — | — | |
| PQDX6 #4 | — | — | — | — | 0.0005 | 0.001 | 0.0025 | 0.0035 | 0.005 | — | |
| Polyquaternium-1 | — | — | — | — | — | — | — | — | — | 0.001 | |
| pH | 7.02 | 7.01 | 7.00 | 7.01 | 7.01 | 7.01 | 6.99 | 7.01 | 7.01 | 7.00 | |
| Osmolality mOsm/kg | 276 | 279 | 272 | 275 | 272 | 273 | 272 | 271 | 273 | 269 | |
| Total Volume | 200 mL | 200 mL | 200 mL | 200 mL | 200 mL | 200 mL | 200 mL | 200 mL | 200 mL | 200 mL | |

$Log_{10}$ Reduction

| Microorganism | Time (hours) | 14762-27A | 14762-27B | 14762-27C | 14762-27D | 14762-27E | 14762-27F | 14762-27G | 14762-27H | 14762-27I | 14762-27J | OPTI-FREE® Express®[a] |
|---|---|---|---|---|---|---|---|---|---|---|---|---|
| C. albicans $7.5 \times 10^{5\,b}$ | 6 | 0.1 | −0.1 | 0.6 | 0.8 | 0.0 | 0.3 | 1.0 | 1.1 | 1.2 | 2.9 | <u>4.9</u>[c] |
| | 24 | 0.0 | 0.4 | 1.2 | 1.6 | 0.6 | 1.3 | 1.7 | 2.0 | 2.4 | 4.0 | <u>4.9</u>[c] |
| S. marcescens $1.0 \times 10^{6\,b}$ | 6 | 0.0 | 2.4 | <u>5.0</u>[c] | <u>5.0</u>[c] | 1.8 | 1.8 | 4.8 | <u>5.0</u>[c] | <u>5.0</u>[c] | <u>5.0</u>[c] | 2.5 |
| | 24 | 1.0 | 4.8 | <u>5.0</u>[c] | <u>5.0</u>[c] | 4.2 | 3.7 | <u>5.0</u>[c] | <u>5.0</u>[c] | 5.0 | <u>5.0</u>[c] | <u>5.0</u>[c] |
| S. aureus $1.2 \times 10^{6\,b}$ | 6 | −0.1 | 3.7 | <u>5.1</u>[c] | 3.1 | <u>5.1</u>[c] | <u>5.1</u>[c] | <u>5.1</u>[c] | <u>5.1</u>[c] | <u>5.1</u>[c] | <u>5.1</u>[c] | 2.7 |
| | 24 | −0.1 | <u>5.1</u>[c] | <u>5.1</u>[c] | 5.1 | <u>5.1</u>[c] | <u>5.1</u>[c] | <u>5.1</u>[c] | <u>5.1</u>[c] | <u>5.1</u>[c] | <u>5.1</u>[c] | 4.8 |

EXAMPLE 5

Representative Preserved Contact Lens Disinfecting Formulation

| Ingredient | w/v % |
|---|---|
| Polymer of Formula (I) | 0.001 |
| Sodium Citrate | 0.56 |
| Citric Acid | 0.021 |
| Sodium Chloride | 0.52 |
| EDTA | 0.05 |
| NaOH/HCl | pH 7 |
| Purified Water | q.s. |

EXAMPLE 6

Representative Preserved Ophthalmic Formulation

| Ingredient | w/v % |
| --- | --- |
| Polymer of Formula (I) | 0.001 |
| Polyoxyl 40 Stearate | 0.1 |
| Boric Acid | 0.25 |
| Sodium Chloride | 0.75 |
| Disodium Edetate | 0.01 |
| NaOH/HCl | q.s., pH = 7.4 |
| Purified Water | q.s. 100% |

The composition above may be prepared by the following method. The batch quantities of boric acid, sodium chloride, disodium edetate, and polyquaternium-1 are weighed and dissolved by stirring in 90% of the batch quantity of purified water. The pH is adjusted to 7.4.+−.0.1 with NaOH and/or HCl. Purified water is added to q.s. to 100%. The mixture is stirred for five minutes to homogenize and then filtered through a sterilizing filter membrane into a sterile recipient.

While the disclosure has been described with reference to a preferred embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from essential scope thereof. Therefore, it is intended that the disclosure not be limited to the particular embodiment disclosed as the best mode contemplated for carrying out this invention, but that the disclosure will include all embodiments falling within the scope of the appended claims.

We claim:

1. A polymer having the formula

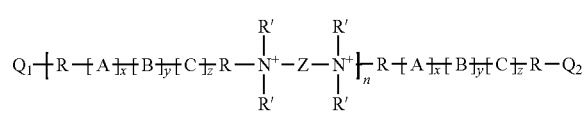

(I)

wherein $[A]_x$, $[B]_y$, and $[C]_z$ are poly(alkylene oxides) each independently selected from the group consisting of poly(ethylene oxide), poly(propylene oxide), and poly(butylene oxide); Z is selected from the group consisting of —CH$_2$CH═CHCH$_2$—, —CH$_2$CH$_2$CH$_2$CH$_2$—, —CH$_2$—C≡C—CH$_2$—, —CH$_2$CH$_2$—O—CH$_2$CH$_2$—, —CH$_2$—N(CH$_2$CH$_2$)$_2$N—CH$_2$—, —CH$_2$CH(OH)CH(OH)CH$_2$— and —CH$_2$—C$_6$H$_4$—CH$_2$—; R is —(CR$_1$R$_2$)$_m$CR$_3$R$_4$— wherein m is an integer from 0 to 3 and R$_1$, R$_2$, R$_3$ and R$_4$ are independently selected from the group consisting of H, CH$_3$ and CH$_2$CH$_3$; n is an integer from 1 to 30; x is either 0 or an integer from 2 to 20; y is an integer from 2 to 20; z is either 0 or an integer from 2 to 20; R' is a branched or unbranched alkyl group having from 1 to 3 carbon atoms and is optionally substituted by one or two hydroxyl groups; Q1 and Q2 are independently selected from the group consisting of —CH$_2$CH═CHCH$_2$—X, —CH$_2$C≡C—CH$_2$—X, —N(R')$_2$, —N(R')$_3$, —N(R')(R''), and —N(R')$_2$(R''), wherein X is a halogen atom and R'' is a benzyl group; and a stoichiometric amount of a pharmaceutically acceptable anion.

2. A polymer according to claim 1 wherein:
at least one of $[A]_x$, $[B]_y$, and $[C]_z$ is poly(butylene oxide); R' is methyl; and Z is —CH$_2$CH═CHCH$_2$—.

3. A polymer according to claim 2 wherein:
x and z are 0; $[B]_y$ is poly(butylene oxide); and y is 4 to 20.

4. A polymer according to claim 3 wherein:
y is 6; m is 2; and R1, R2, R3 and R4 are H.

5. A polymer characterized by a repeat unit having the formula

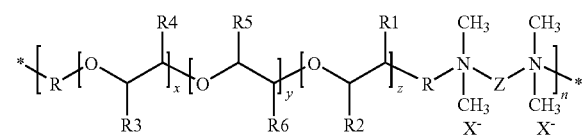

wherein:
Z is selected from the group consisting of —CH$_2$CH═CHCH$_2$—, —CH$_2$CH$_2$CH$_2$CH$_2$—, —CH$_2$—C≡C—CH$_2$—, —CH$_2$CH$_2$—O—CH$_2$CH$_2$—, —CH$_2$—N(CH$_2$CH$_2$)$_2$N—CH$_2$—, —CH$_2$CH(OH)CH(OH)CH$_2$— and —CH$_2$—C$_6$H$_4$—CH$_2$—; R1, R2, R3, R4, R5 and R6 are independently selected from the group consisting of —H, —CH$_3$ and CH$_2$CH$_3$; R is —(CR$_1$R$_2$)$_m$CR$_3$R$_4$— wherein m is an integer from 0 to 3 and R$_1$, R$_2$, R$_3$ and R$_4$ are independently selected from the group consisting of H, CH$_3$ and CH$_2$CH$_3$; x and z are integers from 0 to 20; y is an integer from 2 to 20; n is an integer from 1 to 30; and X is a pharmaceutically acceptable anion.

6. A polymer comprising the condensation product of 1,4-dihalo-2-butene with a monomer of formula

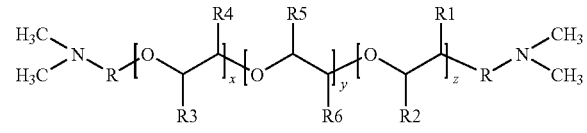

wherein:
R1, R2, R3, R4, R5 and R6 are independently selected from the group consisting of —H, —CH$_3$ and CH$_2$CH$_3$; R is —(CR$_1$R$_2$)$_m$CR$_3$R$_4$— wherein m is an integer from 0 to 3 and R$_1$, R$_2$, R$_3$ and R$_4$ are independently selected from the group consisting of H, CH$_3$ and CH$_2$CH$_3$; x and z are integers from 0 to 20; and y is an integer from 2 to 20.

7. A pharmaceutical composition comprising an preservation-effective amount of a polymer according to claim 1.

8. A pharmaceutical composition comprising an preservation-effective amount of a polymer according to claim 5.

9. A pharmaceutical composition comprising an preservation-effective amount of a polymer according to claim 6.

10. A lens care composition comprising a disinfecting-effective amount of a polymer according to claim 1.

11. A lens care composition comprising a disinfecting-effective amount of a polymer according to claim 5.

12. A lens care composition comprising a disinfecting-effective amount of a polymer according to claim 6.

13. A composition according to claim 7 wherein the polymer is present at a concentration between about 0.00001 and about 1.0 wt %.

14. A composition according to claim 8 wherein the polymer is present at a concentration between about 0.00001 and about 1.0 wt %.

15. A composition according to claim 9 wherein the polymer is present at a concentration between about 0.00001 and about 1.0 wt %.

16. A composition according to claim 1, wherein the composition is an aqueous solution for treating a contact lens, said solution having an osmolality of 250 to 350 milliosmoles/kilogram.

17. A composition according to claim 5, wherein the composition is an aqueous solution for treating a contact lens, said solution having an osmolality of 250 to 350 milliosmoles/kilogram.

18. A composition according to claim 6, wherein the composition is an aqueous solution for treating a contact lens, said solution having an osmolality of 250 to 350 milliosmoles/kilogram.

19. A method of preserving a pharmaceutical composition which comprises including in the composition a preservation-effective amount of a polymer according to claim 1.

20. A method of disinfecting a contact lens which comprises including in the composition a disinfection-effective amount of a polymer according to claim 1.

* * * * *